(12) United States Patent
Mizuno et al.

(10) Patent No.: US 7,459,573 B2
(45) Date of Patent: Dec. 2, 2008

(54) METHOD OF PURIFYING EPOXY COMPOUND

(75) Inventors: Tadashi Mizuno, Ibaraki (JP);
Nobuhiro Arai, Nagaokakyo (JP); Erina Honda, Osaka (JP); Hideo Muraoka, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 5 days.

(21) Appl. No.: 11/889,524

(22) Filed: Aug. 14, 2007

(65) Prior Publication Data
US 2008/0081921 A1    Apr. 3, 2008

(30) Foreign Application Priority Data
Aug. 17, 2006   (JP)   ............... 2006-222794

(51) Int. Cl.
*C07D 301/32*   (2006.01)
(52) U.S. Cl. .................. 549/541; 549/519; 549/560
(58) Field of Classification Search ............... 549/541, 549/519, 560
See application file for complete search history.

(56) References Cited

U.S. PATENT DOCUMENTS 5,405,861 A    4/1995   Itoh et al.
6,884,892 B2   4/2005   Wang et al.

*Primary Examiner*—Janet L Andres
*Assistant Examiner*—David E Gallis
(74) *Attorney, Agent, or Firm*—Foley & Lardner LLP

(57) ABSTRACT

An epoxy compound of the formula (1):

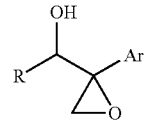

(1)

wherein, R represents a hydrogen atom or an alkyl group having 1 to 12 carbon atoms, and Ar represents an optionally substituted aromatic group, can be purified by dissolving a crude product containing the epoxy compound (1), an aprotic polar solvent and an alkali metal salt in a two-phase solvent composed of water and an organic solvent, which is capable of phase-separating from water, obtaining the organic layer by phase separation, washing with water and then subjecting to isolation of the epoxy compound (1) without decomposition.

13 Claims, 1 Drawing Sheet

METHOD OF PURIFYING EPOXY COMPOUND

TECHNICAL FIELD

The present invention directs to a method of purifying an epoxy compound, more particularly, to method of purifying an epoxy compound without significant decomposition thereof.

BACKGROUND ARTS

Epoxy compounds are useful intermediates capable of being converted into various derivatives. An epoxy compound of the formula (1):

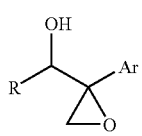

(1)

wherein, R represents a hydrogen atom or an alkyl group having 1 to 12 carbon atoms, and Ar represents an aromatic group optionally substituted with one or more substituents selected from the group consisting of halogen atoms and trifluoromethyl group, (hereinafter, referred to as Epoxy Compound (1)) can be produced, for example, by the following scheme:

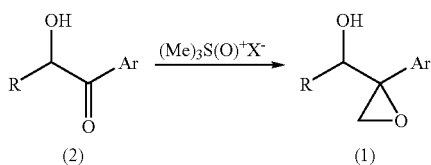

wherein, R and Ar are as defined above. (cf U.S. Pat. Nos. 6,884,892, 5,405,861)

The method, however, has a problem that Epoxy Compound (1) is decomposed when extraction, phase separation and distillation are performed after completion of the reaction.

SUMMARY OF THE INVENTION

The present invention provides a method capable of purifying Epoxy Compound (1) without significant decomposition.

The present invention is a method of purifying Epoxy Compound (1) which comprises dissolving a crude product containing Epoxy Compound (1), an aprotic polar solvent and an alkali metal salt in a two-phase solvent composed of water and an organic solvent, which is capable of phase-separating from water, obtaining the organic layer by phase separation and then subjecting to isolation of Epoxy Compound (1).

That is, the present invention is as described below.

[1] A method of purifying Epoxy Compound (1) which comprises dissolving a crude product containing Epoxy Compound (1), an aprotic polar solvent and an alkali metal salt in a two-phase solvent composed of water and an organic solvent, which is capable of phase-separating from water, obtaining the organic layer by phase separation, washing with water and then subjecting to isolation of Epoxy Compound (1).

[2] The method of purifying Epoxy Compound (1) described in [1], which comprises dissolving a crude product containing Epoxy Compound (1), an aprotic polar solvent and an alkali metal salt in a two-phase solvent composed of water and an organic solvent, which is capable of phase-separating from water, obtaining the organic layer by phase separation, washing with water, concentrating and then subjecting to distillation.

[3] The method of purifying Epoxy Compound (1) described in [1] or [2], which comprises dissolving a crude product containing Epoxy Compound (1), an aprotic polar solvent and an alkali metal salt in a two-phase solvent composed of acidic water and an organic solvent, which is capable of phase-separating from water, obtaining the organic layer by phase separation, washing with water and then subjecting to isolation of Epoxy Compound (1).

[4] The method of purifying Epoxy Compound (1) described in any one of [1] to [3], wherein the washing of the organic layer with water is carried out by using pure water.

[5] The method of purifying Epoxy Compound (1) described in [4], wherein the washing of the organic layer with water is carried out until the electric conductivity of the separated aqueous layer reaches 30 mS/m or less.

[6] The method of purifying Epoxy Compound (1) described in any one of [1] to [5], wherein the organic solvent is an aromatic hydrocarbon.

[7] The method of purifying Epoxy Compound (1) described in any one of [1] to [6], wherein Ar represents a difluorophenyl.

[8] The method of purifying Epoxy Compound (1) described in any one of [1] to [6], wherein Ar represents a 2,4-difluorophenyl or 2,5-difluorophenyl.

[9] The method of purifying Epoxy Compound (1) described in any one of [1] to [8], wherein R represents a methyl.

[10] The method of purifying Epoxy Compound (1) described in any one of [1] to [6], wherein Epoxy Compound (1) is (2R,3R)-3-(2,4-difluorophenyl)-3,4-epoxy-2-butanol or (2R,3R)-3-(2,5-difluorophenyl)-3,4-epoxy-2-butanol.

[11] The method of purifying Epoxy Compound (1) described in any one of [1] to [10], wherein the alkali metal salt is a sodium salt or potassium salt.

[12] The method of purifying Epoxy Compound (1) described in any one of [1] to [11], wherein the aprotic polar solvent is N,N-dimethylformamide (DMF), dimethyl sulfoxide (DMSO) or tetrahydrofuran (THF).

[13] The method of purifying Epoxy Compound (1) described in any one of [1] to [12], wherein the washing of the organic layer with water is carried out until the content of the aprotic polar solvent in the organic layer after washing with water becomes 1 wt % or less.

[14] The method of purifying Epoxy Compound (1) described in any one of [1] to [13], wherein crude product containing Epoxy Compound (1) is a reaction product obtained by allowing an α-hydroxyketone compound of the formula (2):

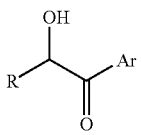

(2)

wherein, R and Ar are as defined above, (hereinafter, referred to as α-Hydroxyketone Compound (2))

to react with a trimethylsulfoxonium salt or trimethylsulfonium salt in the presence of a base in an aprotic polar solvent.

DETAILED DESCRIPTION OF THE INVENTION

Figure 1:
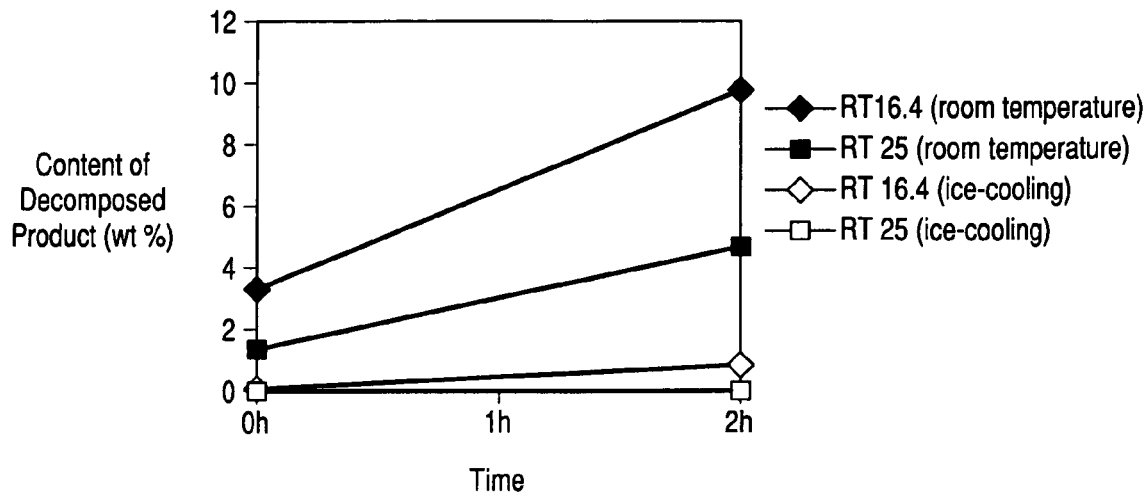
FIG. 1 is a graph showing stability of Epoxy Compound (1) in an alkali aqueous solution under neutralization.

In the present invention, the crude product containing Epoxy Compound (1), an aprotic polar solvent and an alkali metal salt is usually provided by a reaction allowing α-Hydroxyketone Compound (2) to react with a trimethylsulfoxonium salt or trimethylsulfonium salt in the presence of a base in an aprotic polar solvent according to the following scheme:

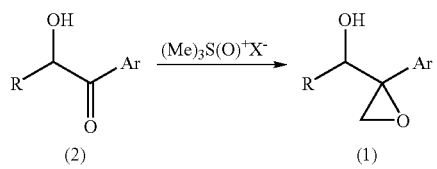

wherein, R and Ar are as defined above.

Examples of the trimethylsulfonium salt include trimethylsulfonium chloride, trimethylsulfonium bromide, trimethylsulfonium iodide and trimethylsulfonium methylsulfate, and preferable are trimethylsulfonium bromide and trimethylsulfonium iodide from the view of easy availability.

Examples of the trimethylsulfoxonium salt are trimethylsulfoxonium chloride, trimethylsulfoxonium bromide, trimethylsulfoxonium iodide and trimethylsulfoxonium methylsulfate, and preferable are trimethylsulfoxonium bromide and trimethylsulfoxonium iodide from the view of easy availability.

The amount of the trimethylsulfoxonium salt or trimethylsulfonium salt used for the reaction is usually 0.8 to 5.0 mol, preferably 1.0 to 3.0 mol, more preferably 1.1 to 2.5 mol based on 1 mol of α-Hydroxyketone Compound (2).

The base is not particularly restricted providing it reacts with a trimethylsulfoxonium salt or trimethylsulfonium salt to produce sulfur ylide, and examples thereof include alkali metal hydroxides such as potassium hydroxide, sodium hydroxide and lithium hydroxide; alkali metal hydrides such as sodium hydride, potassium hydride and lithium hydride; alkylalkali metals such as n-butyllithium, methyllithium and n-hexyllithium; alkali metal amides such as sodium amide, potassium amide, lithium diisopropylamide, lithium dicyclohexylamide and lithium hexamethyldisilazide; and alkali metal alkoxides such as potassium tert-butoxide, sodium tert-butoxide, sodium methoxide, sodium ethoxide, potassium methoxide and potassium ethoxide. Preferable is sodium hydride.

This base may be used in any form, and any methods can be selected for use such as adding a base in the form of powdery solid by portion or the like, preparing a base in the form of solution before addition thereof, dispersing or suspending a base in solvents or mineral oils before dropping thereof, and the like.

The amount of the base used for the reaction is usually 0.25 to 1.1 mol, preferably 0.5 to 1.0 mol, more preferably 0.6 to 0.9 mol based on 1 mol of the trimethylsulfoxonium salt or trimethylsulfonium salt.

The aprotic polar solvent is mentioned below. The amount of the solvent is usually 1 L to 50 L, preferably 4 L to 30 L, more preferably 5 L to 25 L based on 1 kg of α-Hydroxyketone Compound (2).

Addition order of reagents is not particularly restricted, and for example, it may be permissible that a trimethylsulfoxonium salt or trimethylsulfonium salt, and a base are charged in an aprotic polar solvent, then, α-Hydroxyketone Compound (2) is added, alternatively, a trimethylsulfoxonium salt or trimethylsulfonium salt is charged in an aprotic polar solvent, then, a base is added, and to this is added a solution prepared by charging α-Hydroxyketone Compound (2) in an aprotic polar solvent.

This reaction is carried out usually at −40° C. to 120° C., preferably at −20° C. to 60° C., more preferably at −10° C. to 40° C. for usually 0.5 hours to 24 hours, preferably 1 hour to 8 hours.

The present invention is a method of purifying Epoxy Compound (1) from a crude product containing Epoxy Compound (1), an aprotic polar solvent and an alkali metal salt.

In the present invention, the aprotic polar solvent is generally a solvent used for the production of Epoxy Compound (1) and typical examples include ether solvents (e.g., tetrahydrofuran (THF), methyl tert-butyl ether, 1,4-dioxane, diethylene glycol dimethyl ether (diglyme), ethylene glycol dimethyl ether, 1,3-dioxolane, 2-methyltetrahydrofuran), N,N-dimethylformamide (DMF), N,N-dimethylacetamide (DMAc), dimethyl sulfoxide (DMSO), sulfolane, N-methyl-2-pyrrolidinone (NMP), 1,3-dimethyl-2-imidazolidinone (DMI), hexamethylphosphoric amide (HMPA), acetonitrile and propionitrile.

The alkali metal salt is generally by-produced in the process of the production of Epoxy Compound (1) and typical examples include sodium salts (e.g., sodium chloride, sodium iodide, sodium carbonate, sodium hydrogen carbonate, sodium sulfate, sodium hydrogen sulfate, sodium formate, sodium acetate, sodium propionate, sodium oxalate, sodium tartarate, sodium succinate, sodium citrate, sodium malonate) and potassium salts (e.g., potassium chloride, potassium iodide, potassium carbonate, potassium hydrogen carbonate, potassium sulfate, potassium hydrogen sulfate, potassium formate, potassium acetate, potassium propionate, potassium oxalate, sodium potassium tartarate, sodium potassium succinate, sodium potassium malonate).

Examples of "alkyl group having 1 to 12 carbon atoms" represented by R include methyl, ethyl, propyl, isopropyl, butyl, sec-butyl, tert-butyl, pentyl, isopentyl, neopentyl, hexyl, cylohexyl, heptyl, octyl, nonyl, decyl, undecyl and dodecyl. Typical example is methyl.

Examples of the halogen atom in "aromatic group optionally substituted with one or more substituents selected from the group consisting of halogen atoms and trifluoromethyl group" represented by Ar include a fluorine atom, chlorine atom, bromine atom and iodine atom, and among them, a fluorine atom is preferable.

Examples of "aromatic group" in "aromatic group optionally substituted with one or more substituents selected from the group consisting of halogen atoms and trifluoromethyl group" represented by Ar include aryl groups having 6 to 14 carbon atoms such as phenyl and naphthyl; heterocyclic aromatic groups such as pyridyl, pyrimidyl and quinolyl.

When the above-mentioned aromatic group is substituted with one or more substituents selected from the group consisting of halogen atoms and trifluoromethyl group, the number of the substituent is usually 1 to 3.

Specific examples of "aromatic group optionally substituted with one or more substituents selected from the group consisting of halogen atoms and trifluoromethyl group" represented by Ar include phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2,3-difluorophenyl, 2,4-difluorophenyl, 2,5-difluorophenyl, 3,4-difluorophenyl, 3,5-difluorophenyl, 2,6-difluorophenyl, 2,3-dichlorophenyl, 2,4-dichlorophenyl, 2,5-dichlorophenyl, 3,4-dichlorophenyl, 3,5-dichlorophenyl, 2,6-dichlorophenyl, 2,3-dibromophenyl, 2,4-dibromophenyl, 2,5-dibromophenyl, 3,4-dibromophenyl, 3,5-dibromophenyl, 2,6-dibromophenyl, 2,4,6-trifluorophenyl, 2-(trifluoromethyl)phenyl, 3-(trifluoromethyl)phenyl, 4-(trifluoromethyl)phenyl, 1-chloronaphthyl groups (1-chloro-2-naphthyl, 1-chloro-3-naphthyl, 1-chloro-4-naphthyl, 1-chloro-5-naphthyl, 1-chloro-6-naphthyl, 1-chloro-7-naphthyl, 1-chloro-8-naphthyl), 2-chloronaphthyl groups (2-chloro-1-naphthyl, 2-chloro-3-naphthyl, 2-chloro-4-naphthyl, 2-chloro-5-naphthyl, 2-chloro-6-naphthyl, 2-chloro-7-naphthyl, 2-chloro-8-naphthyl), 1-bromonaphthyl groups (1-bromo-2-naphthyl, 1-bromo-3-naphthyl, 1-bromo-4-naphthyl, 1-bromo-5-naphthyl, 1-bromo-6-naphthyl, 1-bromo-7-naphthyl, 1-bromo-8-naphthyl), 2-bromonaphthyl groups (2-bromo-1-naphthyl, 2-bromo-3-naphthyl, 2-bromo-4-naphthyl, 2-bromo-5-naphthyl, 2-bromo-6-naphthyl, 2-bromo-7-naphthyl, 2-bromo-8-naphthyl), 1-fluoronaphthyl groups (1-fluoro-2-naphthyl, 1-fluoro-3-naphthyl, 1-fluoro-4-naphthyl, 1-fluoro-5-naphthyl, 1-fluoro-6-naphthyl, 1-fluoro-7-naphthyl, 1-fluoro-8-naphthyl), 2-fluoronaphthyl groups (2-fluoro-1-naphthyl, 2-fluoro-3-naphthyl, 2-fluoro-4-naphthyl, 2-fluoro-5-naphthyl, 2-fluoro-6-naphthyl, 2-fluoro-7-naphthyl, 2-fluoro-8-naphthyl), 1-trifluoromethylnaphthyl groups (1-trifluoromethyl-2-naphthyl, 1-trifluoromethyl-3-naphthyl, 1-trifluoromethyl-4-naphthyl, 1-trifluoromethyl-5-naphthyl, 1-trifluoromethyl-6-naphthyl, 1-trifluoromethyl-7-naphthyl, 1-trifluoromethyl-8-naphthyl), 2-trifluoromethylnaphthyl groups (2-trifluoromethyl-1-naphthyl, 2-trifluoromethyl-3-naphthyl, 2-trifluoromethyl-4-naphthyl, 2-trifluoromethyl-5-naphthyl, 2-trifluoromethyl-6-naphthyl, 2-trifluoromethyl-7-naphthyl, 2-trifluoromethyl-8-naphthyl), 4-fluoropyridyl groups (4-fluoro-2-pyridyl, 4-fluoro-3-pyridyl) and 3-trifluoromethylpyridyl groups (3-trifluoromethyl-2-pyridyl, 3-trifluoromethyl-4-pyridyl, 3-trifluoromethyl-5-pyridyl, 3-trifluoromethyl-6-pyridyl). Typical examples are difluorophenyl (e.g., 2,4-difluorophenyl, 2,5-difluorophenyl), trifluorophenyl (e.g., 2,4,6-trifluorophenyl) and trifluoromethylphenyl (e.g., 2-(trifluoromethyl)phenyl, 3-(trifluoromethyl)phenyl, 4-(trifluoromethyl)phenyl).

Epoxy Compound (1) has two or more asymmetric carbon atoms, and in the present invention, includes any optically active isomers and mixtures thereof (e.g., racemates, enantiomer mixtures, diastereomer mixtures).

Typical examples of Epoxy Compound (1) include 3-(2,4-difluorophenyl)-3,4-epoxy-2-butanol and 3-(2,5-difluorophenyl)-3,4-epoxy-2-butanol, and examples of their optically active isomers include (2R,3R)-3-(2,4-difluorophenyl)-3,4-epoxy-2-butanol and (2R,3R)-3-(2,5-difluorophenyl)-3,4-epoxy-2-butanol.

In the present invention, the above-mentioned crude product of Epoxy Compound (1) is dissolved in a two-phase solvent composed of water and an organic solvent.

Dissolution into a two-phase solvent may be carried out by adding a reaction mixture into a two-phase solvent, or by adding a two-phase solvent into the mixture, and the former is preferable from the view of operability and stability of Epoxy Compound (1). The addition is carried out usually at 0 to 30° C., preferably at 0 to 10° C. The addition is preferably performed dropwise.

The organic solvent is capable of phase-separating from water and dissolves Epoxy Compound (1). Examples of the organic solvent include halogenated hydrocarbon solvents such as methylene chloride, 1,2-dichloroethane, chloroform, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene and monofluorobenzene; hydrocarbon solvents such as benzene and toluene; and nitrobenzene. Hydrocarbon solvents, especially aromatic hydrocarbon solvents are preferable. Typical preferable example is toluene. Further, a mixed solvent of them may be used, and these solvents may be mixed at any ratio.

The water in a two-phase solvent may be acidic for avoiding decomposition of Epoxy Compound (1).

For making the water acidic, an aqueous mineral acid solution, aqueous organic carboxylic acid solution or the like is used. Here, the aqueous mineral acid solution includes hydrochloric acid, aqueous sulfuric acid and the like./The organic carboxylic acid in the aqueous organic carboxylic acid solution is not particularly restricted providing it is a water-soluble organic carboxylic acid, and includes acetic acid, oxalic acid, tartaric acid, succinic acid, citric acid and the like. Preferable are hydrochloric acid, aqueous tartaric acid solution, aqueous succinic acid solution and aqueous citric acid solution, and particularly preferable are hydrochloric acid and aqueous citric acid solution.

The amount of the acid in the acidic water is preferably 0.1 mol to 1.0 mol, more preferably 0.3 mol to 0.7 mol, particularly preferably 0.3 mol to 0.5 mol based on 1 mol of Epoxy Compound (1). The amount of the acidic water is preferably 0.5 L to 15 L, more preferably 1 L to 10 L, particularly preferably 1 L to 8 L based on 1 kg of Epoxy Compound (1), and preferably 0.5 L to 5 L, more preferably 1 L to 3 L, particularly preferably 1 L to 2 L based on 1 kg of an aprotic polar solvent used for the reaction.

The obtained organic layer by phase separation is washed with water for removing an aprotic polar solvent and an alkali metal salt.

After phase separation, if necessary, the aqueous layer may be extracted with the above-described organic solvent. The organic layer may be washed with an aqueous sodium hydrogen carbonate solution and the like before the subsequent washing with water.

Water to be used for washing can be selected in any qualities and grades such as tap water; however, pure water such as ion-exchanged water and distilled water is preferably used.

The amount of water for washing is usually 0.5 L to 30 L, preferably 1 L to 20 L, more preferably 1 L to 15 L based on 1 kg of Epoxy Compound (1), depending on the content of an aprotic polar solvent and an alkali metal salt. The amount of water is usually 0.1 L to 20 L, preferably 0.5 L to 5 L, more preferably 1 L to 2 L based on 1 kg of an organic solvent, and usually 1000 L to 10000 L, preferably 2000 L to 8000 L, more preferably 3000 L to 6000 L based on 1 kg of an alkali metal salt. Washing with water may be carried out several times dividedly.

Alkali metal salts are collectively called ion components, and the content thereof can be grasped by measuring electric conductivity of an aqueous layer separated in washing with water. Thus, it is preferable that washing is performed until electric conductivity of an aqueous layer to be described later reaches 30 mS/m or less, more preferably 20 mS/m or less, particularly preferably 15 mS/m or less.

Further, the washing is preferably performed until the content of the aprotic polar solvent becomes one part by weight or less, more preferably 0.1 part by weight or less based on 100 parts by weight of the total of Epoxy Compound (1) and the aprotic polar solvent.

After completion of washing with water, the organic layer is subjecting to isolation of Epoxy Compound (1), which is usually performed by concentration and distillation. The concentration is usually distillation off by evaporation of an organic solvent under reduce pressure or ordinary pressure.

The temperature condition in distillation off varies depending on the kind of an organic solvent to be used, and usually 0° C. to 150° C., preferably 20° C. to 100° C., more preferably 20° C. to 70° C. The distillation time is usually 0.5 hours to 24 hours, preferably 1 hour to 18 hours, more preferably 3 to 15 hours, depending on the kind and amount of an organic solvent, and the temperature condition.

The concentrated product is usually subjected to distillation for isolating Epoxy Compound (1). The distillation method can be appropriately selected irrespective of conditions of reduced pressure and ordinary pressure, depending on the boiling point of Epoxy Compound (1), and distillation under reduced pressure is preferable for further ensuring stability. In the case of a lot of coexisting components having higher boiling points, it may be permissible that Epoxy Compound (1) is once fractionally distilled, then, distillation is carried out, using a spinning band distillation apparatus and the like. Here, the temperature condition in distillation is influenced by physical properties of Epoxy Compound (1), and preferably 20° C. to 200° C., more preferably 60° C. to 160° C., particularly preferably 80° C. to 140° C. The distillation time is preferably 0.5 hours to 24 hours, more preferably 1 hour to 15 hours, particularly preferably 3 to 10 hours depending on the kind and amount of Epoxy Compound (1) and the temperature condition. Epoxy Compound (1) can be distilled stably owing to such conditions.

Thus purified Epoxy Compound (1) can be converted into a compound of high added values by chemical derivation and the like. For example, Epoxy Compound (1) can be derived into an epoxy triazole compound according to a method described in U.S. Pat. No. 6,884,892 and the like, further, for example, Epoxy Compound (1) can be derived into a triazole compound or the like useful as an antifungal agent according to a method described in JP-4-356471A or U.S. Pat. No. 5,405,861, and the like.

EXAMPLES

The present invention will be illustrated further in detail by examples below, but the present invention is not limited to them.

(1) Analysis of Chemical Purity (Content) of Epoxy Compound (1)
HPLC Condition
Column: YMC-PACK ODS AM302, 4.6 mm φ×150 mm
Moving phase Liquid A: distilled water or ion-exchanged water
Liquid B: acetonitrile/isopropanol/THF=75/20/5 (v/v/v)
Gradient Condition:

TABLE 1

| | Time (min.) | | | | | | |
|---|---|---|---|---|---|---|---|
| | 0 | 20 | 30 | 30.01 | 35 | 35.01 | 45 |
| Liquid B moving phase concentration (%) | 20 | 20 | 55 | 90 | 90 | 20 | stop |

Flow rate: 1.0 mL/min
Column temperature: 35° C.
Detection wavelength: UV 254 nm
Sample dilution liquid: acetonitrile/ion-exchanged water (or distilled water)=9/1 (v/v)
Injection amount: 15 μL About 0.2 mL of a sample was dissolved in about 10 mL of diluent to give a specimen solution, and 15 μL of this was injected into HPLC, and analyzed. The retention time in the case of (2R,3R)-3-(2,4-difluorophenyl)-3,4-epoxy-2-butanol was about 19 minutes, and was about 19 minutes also in the case of (2R,3R)-3-(2,5-difluorophenyl)-3,4-epoxy-2-butanol.

(2) Analysis of Content of Aprotic Polar Solvent
Measurement was performed on the organic layer after washing with water.
GC Condition (in the Case of Dimethyl Sulfoxide (DMSO))
Column: G-100 φ1.2 mm×40 mm, 2.0 μm
Carrier gas: nitrogen
Flow rate: 10 mL/min
Column temperature: 80° C. (20 min.)→[temperature rising 30° C./min.]→200° C. (5 min.)
Injection temperature: 200° C.
Detector temperature: 200° C.
Detection method: FID
Sample dilution liquid: acetonitrile
Injection amount: 1 μL
Analysis parameter

TABLE 2

| Width: | 5 | Slope: | 500 |
|---|---|---|---|
| Drift: | 0 | Min. area: | 500 |
| T. DBL: | 0 | Stop time: | 20 |

Twenty milligrams (20 mg) of DMSO was weighed precisely, and acetonitrile was added to prepare a standard solution having a volume correctly controlled to 10 mL. On the other hand, 1 g of the sample was weighed precisely, and dissolved in acetonitrile to prepare a specimen solution having a volume correctly controlled to 10 mL. Each 1 μL of the standard solution and the specimen solution was injected in GC, and analyzed, respectively, and the content of DMSO was quantified by the following formula. The retention time in the case of aprotic polar solvent dimethyl sulfoxide (DMSO) was about 16 minutes, and detection limit under this condition was 14 ppm.

(Quantification Calculation Formula of DMSO Content)

Content (%) of DMSO=(DMSO peak area of sample solution×weight (mg) of DMSO used for preparation of standard solution)/(DMSO peak area of standard solution×weight (mg) of sample solution)×100(%)

(3) Analysis of Content of Alkali Metal Salt (Ion Component)

The electric conductivity of an aqueous layer separated in washing an organic layer with water was measured.
Electric Conductivity Measurement Condition
Apparatus: conductivity meter (Horiba Custoney ACT)
Temperature: room temperature An electrode was immersed in the specimen sample, and measurement and analysis were performed.

Production Example 1

According to a method described in Patent document 3, a reaction mixture of (2R,3R)-3-(2,4-difluorophenyl)-3,4-epoxy-2-butanol was prepared by the following method.

To a solution composed of 20.93 kg of dimethyl sulfoxide (DMSO) and 7.12 kg of tetrahydrofuran (THF), trimethylsulfoxonium iodide (4.893 kg, 22.23 mol) was added, and then, sodium hydride (60% oil dispersed product, 730 g, 17.57 mol) dispersed in 1.45 kg of liquid paraffin was added at room temperature. After termination of generation of hydrogen, a solution of (2R)-2',4'-difluoro-2-hydroxypropiophenone (3.338 kg, 17.93 mol) in DMSO (8.81 kg) was dropped slowly at 0 to 5° C., and the mixture was stirred for about 5 hours at the same temperature, to give a reaction mixture of (2R,3R)-3-(2,4-difluorophenyl)-3,4-epoxy-2-butanol. Production Example 2 (2R,3R)-3-(2,5-difluorophenyl)-3,4-epoxy-2-butanol was prepared in the same manner as in Production Example 1 excepting that (2R)-2',4'-difluoro-2-hydroxypropiophenone was substituted by (2R)-2',5'-difluoro-2-hydroxypropiophenone in Production Example 1.

Example 1

The reaction mixture (13.17 kg; containing 1 kg of (2R,3R)-3-(2,5-difluorophenyl)-3,4-epoxy-2-butanol, 8.78 kg of DMSO, 1.98 kg of THF, 650 g of alkali metal salt) obtained in the method of Production Example 2 was dropped into a two phase solvent composed of hydrochloric acid having a concentration of 1 wt % (hydrogen chloride 71.0 g: corresponding to 1.95 mol) and 3.5 L of toluene cooled to 5° C., while stirring, so that the upper limit of the reaction temperature was 25° C., and after dropping, the mixture was stirred at around 20° C. (the aqueous layer had a pH of 2.1, in this operation). After allowing to stand still, the organic layer and the aqueous layer were separated, and to this aqueous layer was added 3.5 L of toluene and the mixture was stirred, allowed to stand still and subjected to liquid separation at around 20° C., further, to the resulting aqueous layer was added again 1.8 L of toluene and the mixture was stirred, allowed to stand still and subjected to liquid separation at around 20° C.

The resultant three organic layers were combined into one portion, and a separately prepared solution composed of 21.0 g (0.25 mol) of sodium hydrogen carbonate and 3.5 L of tap water was added to this and washing (stirring, standing still, liquid separation) was performed at around 20° C. (aqueous layer had a pH of 8.5 in this operation). Then, the organic layer was washed (stirring, standing still, liquid separation) three times in total with 3.5 L of ion-exchanged water (electric conductivity: 0.2 mS/m), to give a solution of (2R,3R)-3-(2,5-difluorophenyl)-3,4-epoxy-2-butanol in toluene. In this operation, DMSO was not detected from the organic layer (detection limit: less than 14 ppm), and the electric conductivity of the last aqueous layer washed with ion-exchanged water was 2.0 mS/m.

Next, the aqueous layer was concentrated under reduced pressure over about 2.5 hours under conditions of up to an absolute pressure of 2.6 kPa/an internal temperature of 65° C. to distill toluene and THF off, then, distilled under reduced pressure over about 4 hours under conditions of up to an absolute pressure of 0.27 kPa/an internal temperature of 140° C. to, to obtain 830 g of purified (2R,3R)-3-(2,5-difluorophenyl)-3,4-epoxy-2-butanol (yield: 83%).

Example 2

Eight hundred and thirty grams (830 g) of purified (2R,3R)-3-(2,5-difluorophenyl)-3,4-epoxy-2-butanol (yield: 83%) was obtained by the same operation as in Example 1 excepting that the aqueous acidic solution in Example 1 was changed from hydrochloric acid to a citric acid aqueous solution (citric acid: 374.7 g, corresponding to 1.95 mol).

The DMSO content of the organic layer after washing with water was smaller than the detectable limit (less than 14 ppm), and the electric conductivity of the last aqueous layer washed with ion-exchanged water was 0.5 mS/m.

Example 3

Eight hundred and thirty grams (830 g) of purified (2R,3R)-3-(2,4-difluorophenyl)-3,4-epoxy-2-butanol (yield: 83%) was obtained by the same operation as in Example 2 excepting that 13.2 kg of the reaction mixture obtained in the method of Production Example 1 (corresponding to 1 kg of (2R,3R)-3-(2,4-difluorophenyl)-3,4-epoxy-2-butanol, 8.78 kg of DMSO, 1.98 kg of THF, 650 g of alkali metal salt) was used, and the temperature of dropping into the two phase solvent composed of toluene and aqueous citric acid solution was set lower than the upper limit of 10° C.

The DMSO content of the organic layer after washing with water was smaller than the detectable limit (less than 14 ppm), and the electric conductivity of the last aqueous layer washed with ion-exchanged water was 0.5 mS/m.

Example 4

Eight hundred and thirty grams (830 g) of purified (2R,3R)-3-(2,4-difluorophenyl)-3,4-epoxy-2-butanol (yield: 83%) was obtained by the same operation as in Example 3 excepting that the aqueous citric acid solution in Example 3 was replaced by an aqueous tartaric acid solution (tartaric acid: 292.7 g, corresponding to 1.95 mol).

The DMSO content of the organic layer after washing with water was smaller than the detectable limit (less than 14 ppm), and the electric conductivity of the last aqueous layer washed with ion-exchanged water was 0.5 mS/m.

Reference Example 1

Epoxy Compound (1) was dropped into a mixed solvent composed of 7.5 L of water and 3.5 L of toluene cooled to 5° C., over about 1 hour so that the upper limit was 25° C. (in this operation, the aqueous layer had a pH value of 12 and then this solution is supposed to be neutralized to a pH value of 6.8 over about 5 hours using 35% hydrochloric acid water) to find increase in peak (shown in FIG. 1) of decomposed materials (RT 16.4 and RT 25) and reduction of the content of (2R,3R)-

3-(2,5-difluorophenyl)-3,4-epoxy-2-butanol down to about 80%. The subsequent operation was carried out in the same manner as in Example 1, and purification by distillation was performed, to obtain 600 g (recovery ratio: 60%) of (2R,3R)-3-(2,5-difluorophenyl)-3,4-epoxy-2-butanol containing decomposed materials.

Reference Example 2

Figure 2:
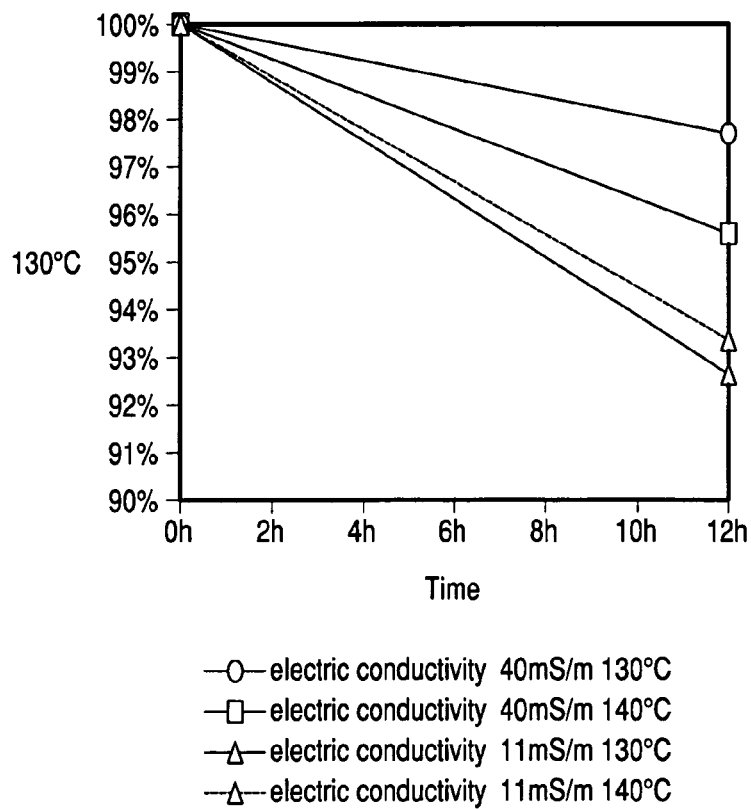
FIG. 2 is a graph showing stability of Epoxy Compound (1) versus electric conductivity in an aqueous layer after washing of Epoxy Compound (1) with water.

The number of organic layer washing using 3.5 L of ion-exchanged water (electric conductivity: 0.2 mS/m) in Example 1 was changed from three times to once, to find an electric conductivity of the washed aqueous layer of 40 mS/m. The subsequent operation was carried out in the same manner as in Example 1, and heating stabilities of the concentrated material of Epoxy Compound (1) after performing concentration under reduced pressure of the organic layer and the concentrated material of the organic layer after washing with water obtained in Example 1 (washing with ion-exchanged water: three times in total, electric conductivity: 2.0 mS/m) at temperature levels of 130° C. and 140° C., respectively, to resultantly find a tendency of remarkable deterioration of Epoxy Compound (1) in the former case (shown in FIG. 2).

According to the present invention, Epoxy Compound (1) useful as a synthesis intermediate can be efficiently purified without decomposition by an industrially advantageous means.

The invention claimed is:

1. A method of purifying an epoxy compound of the formula (1):

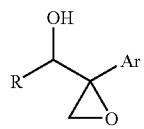

(1)

wherein, R represents a hydrogen atom or an alkyl group having 1 to 12 carbon atoms, and Ar represents an aromatic group optionally substituted with one or more substituents selected from the group consisting of halogen atoms and trifluoromethyl group,
which comprises dissolving a crude product containing the epoxy compound of the formula (1), an aprotic polar solvent and an alkali metal salt in a two-phase solvent composed of water and an organic solvent, which is capable of phase-separating from water, obtaining the organic layer by phase separation, washing with water, concentrating and then subjecting to isolation of the epoxy compound of the formula (1) by distillation.

2. The method of purifying the epoxy compound of the formula (1) according to claim 1, wherein the washing of the organic layer with water is carried out by using pure water.

3. The method of purifying the epoxy compound of the formula (1) according to claim 1, which Ar represents a difluorophenyl.

4. The method of purifying the epoxy compound of the formula (1) according to claim 1, wherein Ar represent a 2,4-difluorophenyl or 2,5-difluorophenyl.

5. The method of purifying the epoxy compound of the formula (1) according to claim 1, wherein R represents a methyl.

6. The method of purifying the epoxy compound of the formula (1) according to claim 1, wherein the epoxy compound of the formula (1) is (2R,3R)-3-(2,4-difluorophenyl)-3,4-epoxy-2-butanol or (2R,3R)-3-(2,5-difluorophenyl)-3,4-epoxy-2-butanol.

7. The method of purifying the epoxy compound of the formula (1) according to claim 1, wherein the alkali metal salt is a sodium salt or potassium salt.

8. The method of purifying the epoxy compound of the formula (1) according to claim 1, wherein the aprotic polar solvent is N,N-dimethylformamide, dimethyl sulfoxide or tetrahydrofuran.

9. The method of purifying the epoxy compound of the formula (1) according to claim 1, wherein crude product containing the epoxy compound of the formula (1) is a reaction product obtained by allowing an α-hydroxyketone compound of the formula (2):

(2)

wherein, R and Ar are as defined in claim 1,
to react with a trimethylsulfonium salt or trimethysulfonium salt in the presence of a base in an aprotic polar solvent.

10. The method of purifying the epoxy compound of the formula (1)

(1)

wherein, R represents a hydrogen atom or an alkyl group having 1 to 12 carbon atoms, and Ar represents an aromatic group optionally substituted with one or more substituents selected from the group consisting of halogen atoms and trifluoromethyl group,
which comprises dissolving a crude product containing the epoxy compound of the formula (1), an aprotic polar solvent and an alkali metal salt in a two-phase solvent composed of acidic water and an organic solvent, which is capable of phase separating from water, obtaining the organic layer by phase separation, washing with water and then subjecting to isolation of the epoxy compound of the formula (1).

11. The method of purifying the epoxy compound of the formula (1):

(1)

wherein, R represents a hydrogen atom or an alkyl group having 1 to 12 carbon atoms, and Ar represents an aromatic group optionally substituted with one or more substituents selected from the group consisting of halogen atoms and trifluoromethyl group, which comprises dissolving a crude product containing the epoxy compound of the formula (1), an aprotic polar solvent and an alkali metal salt in a two-phase solvent composed of water and an organic solvent, which is capable of phase-separating from water, obtaining the organic layer by phase separation, washing with pure water and then subjecting to isolation of the epoxy compound of the formula (1), wherein the washing of the organic layer with pure water is carried out until the electric conductivity of the separated aqueous layer reaches 30 mS/in or less.

12. The method of purifying the epoxy compound of the formula (1):

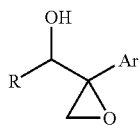
(1)

wherein, R represents a hydrogen atom or an alkyl group having 1 to 12 carbon atoms, and Ar represents an aromatic group optionally substituted with one or more substituents selected from the group consisting of halogen atoms and trifluoromethyl group, which comprises dissolving a crude product containing the epoxy compound of the formula (1), an aprotic polar solvent and an alkali metal salt in a two-phase solvent composed of water and an organic solvent, which is capable of phase-separating from water, obtaining the organic layer by phase separation, washing with water and then subjecting to isolation of the epoxy compound of the formula (1), wherein the organic solvent is an aromatic hydrocarbon.

13. The method of purifying the epoxy compound of the formula (1):

(1)

wherein, R represents a hydrogen atom or an alkyl group having 1 to 12 carbon atoms, and Ar represents an aromatic group optionally substituted with one or more substituents selected from the group consisting of halogen atoms and trifluoromethyl group, which comprises dissolving a crude product containing the epoxy compound of the formula (1), an aprotic polar solvent and an alkali metal salt in a two-phase solvent composed of water and an organic solvent, which is capable of phase-separating from water, obtaining the organic layer by phase separation, washing with water and then subjecting to isolation of the epoxy compound of the formula (1), wherein the washing of the organic layer with water is carried out until the content of the aprotic polar solvent in the organic layer after washing with water becomes 1 wt% or less.

* * * * *